Figure 1A:
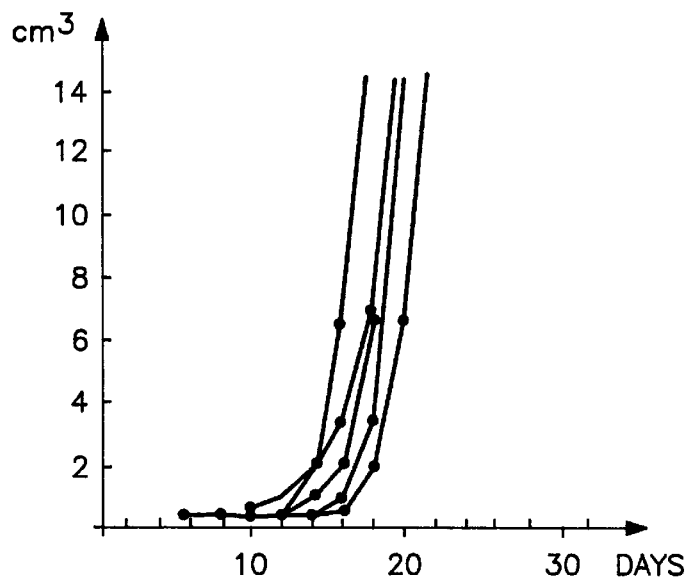

United States Patent [19]
Roth et al.

[11] Patent Number: 6,074,637
[45] Date of Patent: Jun. 13, 2000

[54] CELLULAR COMPOSITION FOR THE TREATMENT OF HUMAN OR ANIMAL ORGANISMS

[75] Inventors: Claude Roth, Paris; Lluis M. Mir, Verrieres le Buisson; Philippe Kourilsky, Paris, all of France

[73] Assignees: Institut Pasteur; Institut National de la Sante et de la Recherche Medicale, both of Paris Cedex, France

[21] Appl. No.: 08/485,160

[22] Filed: Jun. 7, 1995

Related U.S. Application Data

[63] Continuation of application No. 08/087,809, filed as application No. PCT/FR92/01061, Nov. 13, 1992, abandoned.

[30] Foreign Application Priority Data

Nov. 15, 1991 [FR] France ................................. 91 14119

[51] Int. Cl.[7] .................................................. A01N 63/00
[52] U.S. Cl. ....................................................... 424/93.21
[58] Field of Search ........................... 424/184.1, 93.21; 435/172.3, 240.2, 69.1; 935/62, 65

[56] References Cited

U.S. PATENT DOCUMENTS

| | | | |
|---|---|---|---|
| 4,783,407 | 11/1988 | Provost et al. | 435/235 |
| 5,219,740 | 6/1993 | Miller et al. | 435/69.6 |
| 5,358,866 | 10/1994 | Mullen et al. | 435/240.2 |

FOREIGN PATENT DOCUMENTS

| | | | |
|---|---|---|---|
| WO90/06997 | 6/1990 | WIPO . | |
| WO92/05262 | 4/1992 | WIPO . | |
| WO 93/07887 | 4/1993 | WIPO | A61K 37/00 |

OTHER PUBLICATIONS

Gutierrez et al., The Lancet vol. 339, pp. 715–721.
Ledley et al., Human Gene Therapy 2: 77–83 (1991).
Sasada et al, Cell Structure and Function 12, 205–217 (1987).
Selden et al., Science, vol. 236, May 8, 1987, pp. 714–718.
Gupta et al., Transplantation, vol. 50, No. 3 (Sep. 1990) pp. 472–475.
Buberik et al, Immunol. Lett. 23 (1990) pp. 287–292.
Gansbacher et al. J. Exp. Med., vol. 172 (Oct. 1990) pp. 1217—1224.
Asher et al., J. Immunol., vol. 146 No. 9 (May 1, 1991) pp. 3227–3234.
Moolten, Cancer Res. vol. 46 (Oct. 1986) pp. 5276–5281.
DB Moody et al. (1991) J Urology 145 (4 supp): 293A.
PT Golumbek et al (1991) Science 254:713–716.
R Dijkema et al (1985) EMBO J 4: 761–767.
PW Gray et al (1982) Nature 295: 503–508.
U Reinhold et al (1991) Cancer 68: 2155–2160.
T Yokota et al (1985) Proc Natl Acad Sci USA 82: 68–72.
R Reeves et al (1986) Proc Natl Acad Sci USA 83: 3228–3232.
JM Wilson et al (1989) Science 244: 1344–1346.
J Bubenik et al (1991) J Exp Clin Cancer Res 10:213–220.

*Primary Examiner*—Bruce R. Campbell
*Attorney, Agent, or Firm*—Jacobson, Price, Holman & Stern, PLLC

[57] ABSTRACT

Composition designed to treat human or animal organisms comprising cells expressing genes enabling them to secrete in vivo one or more biologically-active substances, said cells exhibiting genetic characteristics preventing them from growing durably in the treated organism, and making them susceptible to elimination artificially or naturally from the organism. These compositions can be used in particular in the treatment of tumors or cancers, in which case the substances used are interleukins. The cells contained in these compositions are at least partially allogenic or xenogenic.

29 Claims, 5 Drawing Sheets

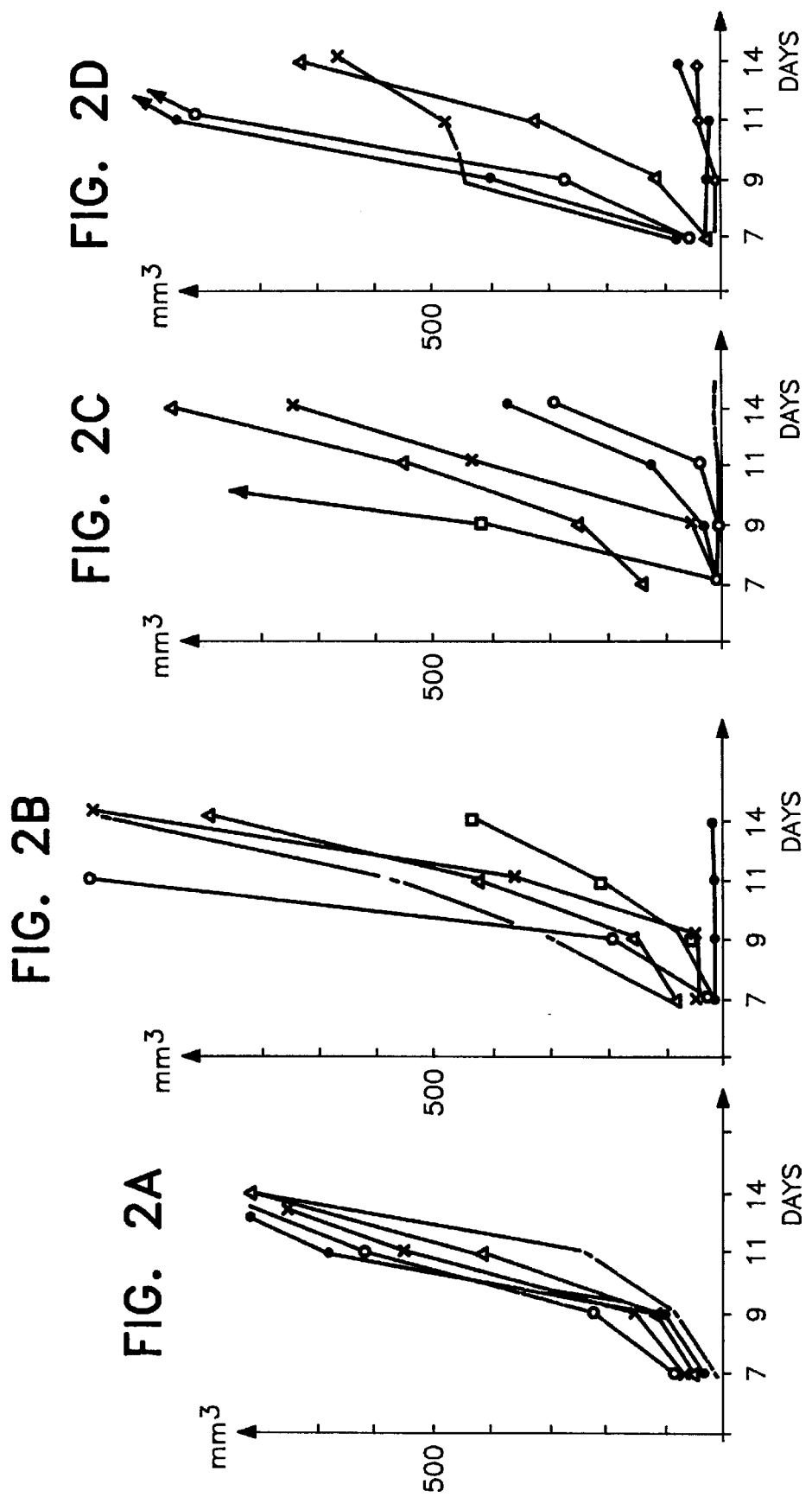

CELLULAR COMPOSITION FOR THE TREATMENT OF HUMAN OR ANIMAL ORGANISMS

This application is a continuation of application Ser. No. 08/087,809, filed Jul. 15, 1993, abandoned, which was the National Stage of International Application PCT/FR92/01061, filed Nov. 13, 1992.

The present invention has for object a cellular composition for the treatment of human or animal organisms.

It was very recently established, by various scientific teams, that the local injection, in organisms affected by a tumor, of syngenic tumoral cells secreting an interleukin allowed the rejection of these tumors by the organism.

This was demonstrated for interleukin-2 by Bubenik et al (Immunol.Letters, 10 279–282 (1988), Immunol.Letters, 23 287–292 (1989)) and confirmed in particular by Fearon et al (Cell., 60 397–403 (1990)) and Ley et al (Eur.J.of Immunol., 21 851–854 (1991), Res.Immunol., 141 855–863 (1990)).

The authors of these articles mention that rejection is accompanied by a memorization of the response. The animal is thus vaccinated against the subsequent growth of a tumor of the same type, even is this has been grafted to a different site.

Syngenic cancer cells producing interleukin-4 have also been tested with identical results, as reported by Golumbek (Science, 254 713–716 (1991) and Tepper et al (Cell., 57 503–512 (1989)) as well as cells secreting the tumor necrosis factor (TNF) as described by Blankenstein et al (J.Exp.Med., 173 1047–1052 (1991)).

The systems described in these publications nevertheless present drawbacks to their use in human therapy.

In all these publications, in fact, the cells secreting the interleukins are cells of the individual or of a syngenic individual, which have been modified to express interleukins.

In human therapy, the major drawback of this methodology stems from the fact that the cells expressing interleukin and injected into the organism are liable to continue to grow even after the tumor has been rejected.

A second drawback of the techniques described in the prior art resides in the method of insertion of the DNA coding for interleukins, which is often based on the use of viral and particularly retroviral vectors.

These methods display a high effectiveness of DNA transmission, but the use of virus and particularly retrovirus could present serious drawbacks in connection with human therapy.

These methods also often demand a rigorous selection of the transfectants over a long period of time, and are accordingly difficult to apply on a large scale in human therapy in particular.

To the best of the knowledge of the applicants, the prior art hence does not contain reliable techniques, easy to apply, and compatible with the requirements of human health, serving to treat tumors or cancers by cells synthesizing interleukins.

The main problem resides in a possible survival and a possible growth in the treated organism of the injected cells coding for the interleukins or of viruses derived from viruses used as vectors.

The applicants are therefore concerned with the use of compositions serving to treat transiently human or animal organisms by biologically-active substances not presenting the above-mentioned drawbacks.

They have demonstrated in a striking manner that use could be made of lines of non-syngenic cells, and particularly of lines of allogenic cells secreting biologically-active substances, to treat said organisms. They have thus demonstrated, in particular, that the use of non-syngenic cells allowed a transient secretion of interleukin in said organisms.

The present invention therefore has for object a composition intended to treat human or animal organisms, comprising cells expressing genes enabling them to secrete in vivo one or more biologically-active substances, wherein said cells exhibit genetic characteristics preventing them from growing durably in the treated organism and making them susceptible to be eliminated artificially or naturally from the organism.

These biologically-active substances can in particular be intended to treat transiently organisms affected by a tumor or a cancer, in which case said substances may be interleukins. The cells are accordingly selected so as to be eliminated after the disappearance or during the regression of the tumor or of the cancer.

These substances may also be molecules capable of inducing an immune reaction of the humoral or cellular type, such as, for example, the antigen HbS described in French Patent No.80.09.041, a fragment of glycoprotein from the envelope of HIV virus or any other antigen of viral or bacterial origin, or even any normal or mutant antigen implicated in pathologies, for example, tumor-specific antigens, or implicated in auto-immune diseases, or even antibodies or derivatives of specific antibodies. Besides their use in the field of vaccination or immunotherapy, these cells can also help to deliver transiently other active substances, such as hormones, growth factors or their fragments.

The cells are selected so that the treated organisms possess an immune system allowing their elimination. Thus, the cells are not totally syngenic, but are at least partially allogenic. The expression cell at least partially allogenic means a cell which is distinguished from its recipient host organisms by at least one HLA determinant.

The cells may also be xenogenic, although this type of cell may present the drawback of being rejected more rapidly and of secreting a smaller amount of substances.

But it is also possible to modify the allogenic or xenogenic cells to make them express antigens characteristic of human cells, for example Class I or Class II HLA antigens, and to give them partially syngenic characteristics so as to stimulate transiently the characteristic immune response of the host.

A particularly suitable cell line is the VERO line issuing from a species of monkey. In fact, these cells offer the advantage of having been designed and used by several teams (see in particular *VERO cells, Origin, Properties and Biomedical Applications*, Bunsiti Simizu and Toyozo Terasima, published by the Department of Microbiology of the Medical School of the University of Chiba (Japan). Thus, their genetics are fairly well known, making it possible to reduce the risks of infection due to endogenous viruses or retroviruses. This is particularly advantageous in connection with human therapy.

The cells of the composition according to the invention may also be sensitive to a drug, thus facilitating their elimination by the introduction of said drug into the organism. One such drug may be gancyclovir, to which the cells carrying the gene of thymidine kinase of the herpes virus are sensitive.

Said immunomodulators may be in particular IL-2, IL-4, TNF (tumor necrosis factor), gamma interferon, and/or GM-CSF (granular monocytic colony stimulating factor).

The cells may secrete these substances alone or in combination. These substances are preferably produced in synergistic quantities. Advantageously, such a composition secretes IL-2 and IL-4 in synergistic quantities.

Furthermore, the cells of this composition can carry an easily-identifiable dye marker. This could be, for example, a gene coding for luciferase or β-galactosidase.

To reinforce the transient character of the expression of the biologically-active substances and in particular of the immunomodulators in the treated organisms, the genes enabling the cells to secrete these substances can be introduced into the cells by transfection, and particularly by transfection without subsequent selection of stable transfectant. A pool of cells is obtained, mainly composed of cells transfected by DNA, in which the latter is not integrated. In this way, the genes, and particularly those coding for the interleukins, are expressed, but their corresponding DNA is rapidly eliminated during the division cycles. This helps to reinforce the transient character of the expression of the substances in the treated organisms.

Transfection consists of the introduction of nu DNA into cells. This is a technique known in itself and described in particular in the technical manual of Maniatis et al (*Molecular Cloning, A Laboratory Manual*, Cold Spring Harbor Laboratory, 1982).

One can in particular make use of precipitation with calcium phosphate, electroporation, and occasionally preparations of liposomes such as the commercial preparation Lipofection Reagent (Bethesda Research Laboratories, Life Technologies Inc).

The genes carrying the immunomodulators can be obtained by cloning, from cell DNA in particular, or by synthesis. For IL-2 and IL-4 in particular, the DNA preparations described in Karasuyama et al (Eur.J.Immunol., 18 97 (1988)) can be employed.

Furthermore, the cells used in the composition according to the invention can possess genes enabling them to secrete specific antigens of the tumor or of the cancer to be treated, in order to augment the response of the organism to these antigens.

Further quantities of tumor antigen can also be introduced by addition to the cells secreting the interleukins of chemically-synthesized antigen.

The composition according to the invention may comprise several cell types, each cell type expressing an immunomodulator, or may consist of a single cell type secreting one or more immunomodulators. The invention also concerns any treatment in which an active substance can be usefully delivered in vivo transiently by manipulated cell lines that are at least partially allogenic or xenogenic.

For reasons of simplicity of use, it may also be interesting to prepare cell lines which only express a single interleukin. However, it may also be advantageous for the same cells to secrete combinations of interleukins.

Furthermore, the present invention concerns in particular the use of the cells thus defined for the fabrication of a medicinal product for the treatment of human or animal organisms affected by a tumor or a cancer, as well as medicinal products or vaccines containing said cells.

Note, furthermore, that such compositions are preferably intended for use in the form of local injections, but are also susceptible to systemic use. Repeated injections can be administered, although their efficacy could deteriorate as the number of injections increases, owing to accelerated rejection by the immune system.

The quantities of interleukins produced by these cells must be adjusted according to the type of tumor. As an example, an expression of about 4000 international units of IL-2/ml·$10^6$ cells is effective in the case described below.

Nevertheless, for slow-growing tumors, smaller doses can be effective.

The present compositions are preferably used in the treatment of solid tumors, but can also be used in the treatment of any other type of tumor or cancer.

Figure 1B:
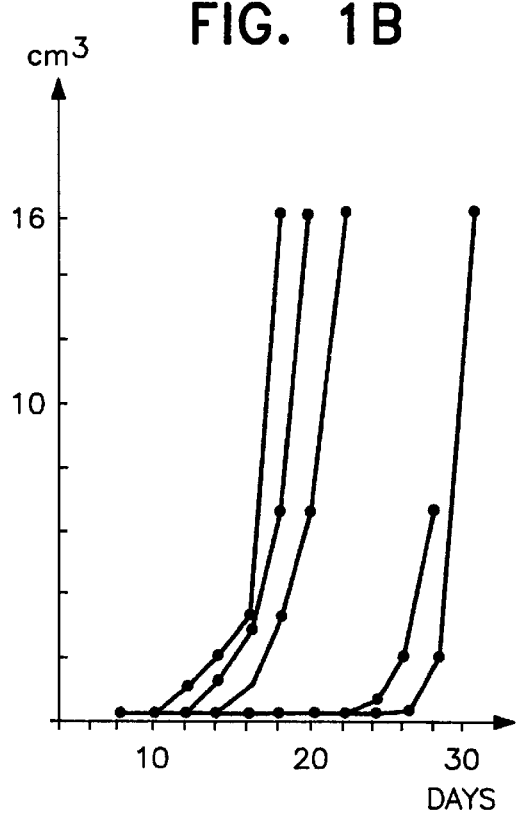
Figure 1C:
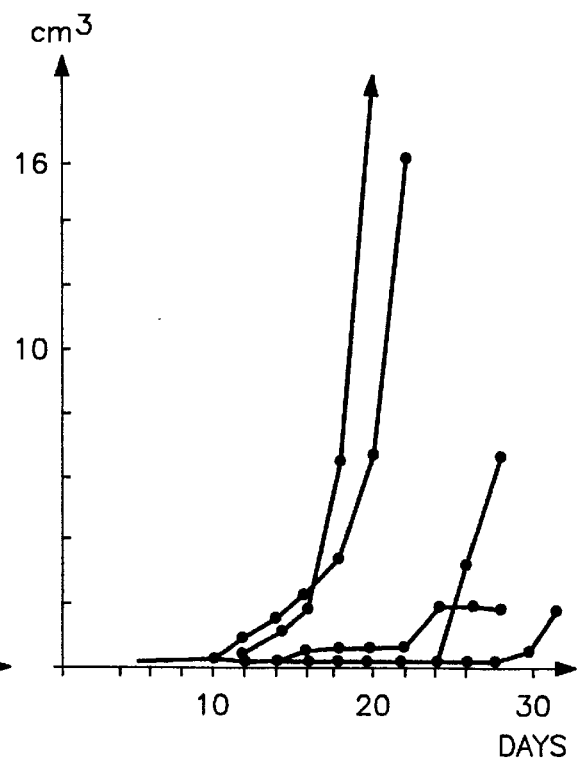
Figure 1E:
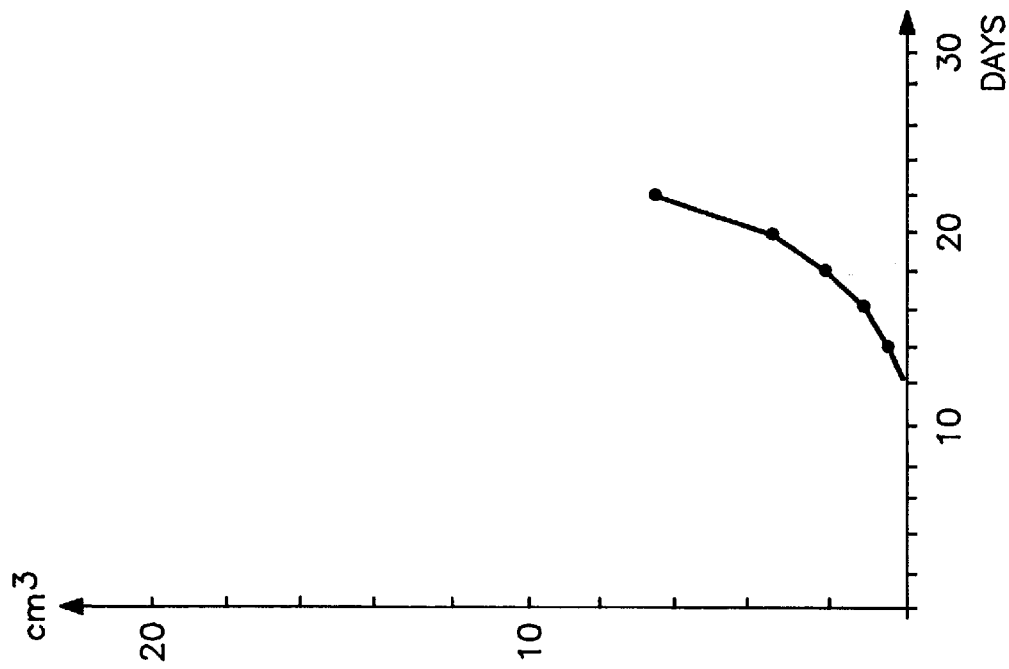
Figure 1D:
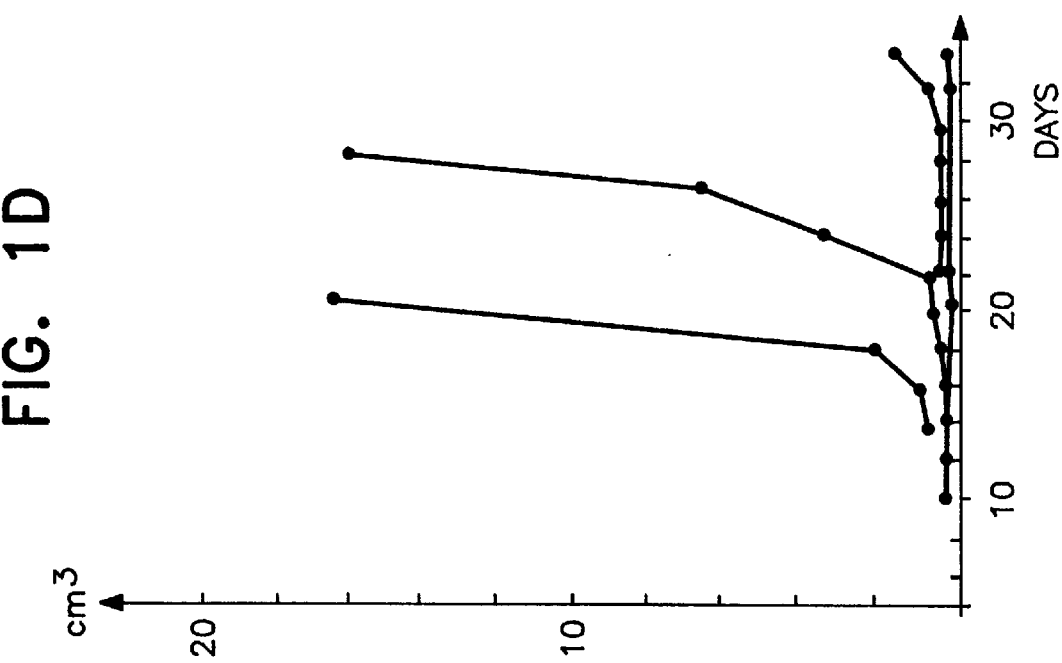

The present invention is illustrated, but without limitation, by the following examples of use in which:

FIGS. 1A to 1E are curves illustrating the growth of tumor cells in the absence of allogenic cells (FIG. 1A), in the presence of allogenic cells not secreting IL-2 (FIGS. 1B and 1C), and in the presence of allogenic cells secreting IL-2 (FIGS. 1D and 1E).

Figure 2E:
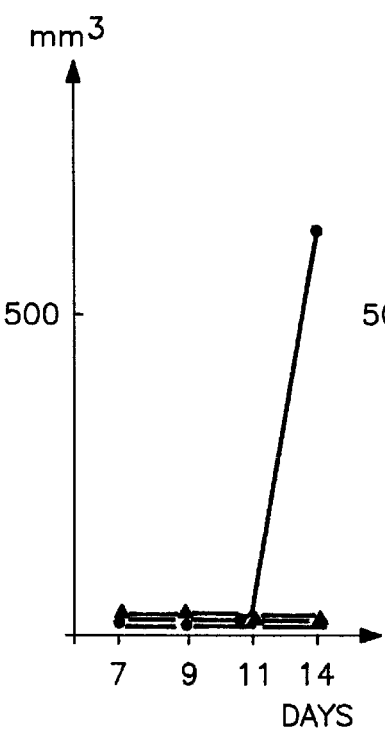
Figure 2F:
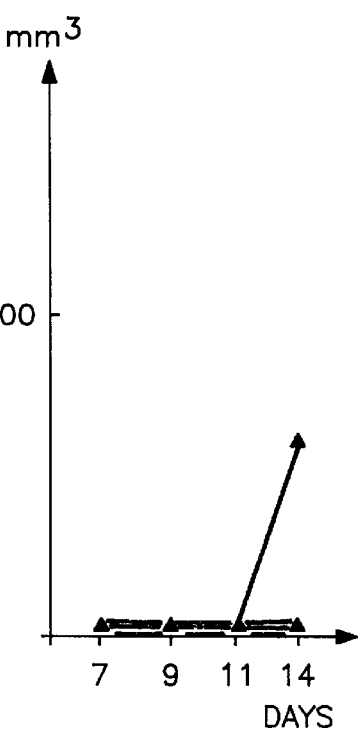
Figure 2G:
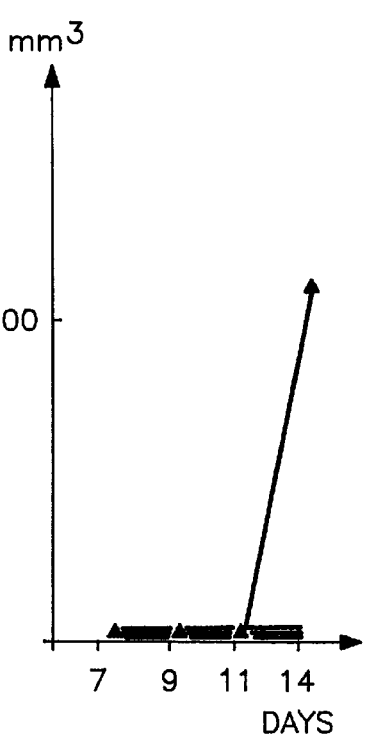

FIGS. 2A to 2I show the effect of cells secreting interleukins on the rejection of freshly-implanted Lewis tumors. FIG. 2A is a control without injection of any allogenic cell. FIGS. 2B to 2D correspond to the injection of increasing doses of P815 non-transfected cells. FIGS. 2E to 2G correspond to the injection of P815 cells secreting IL-2, while FIGS. 2H and 2I correspond to the injection of P815 cells respectively synthesizing IL-4 and a combination of cells synthesizing IL-2 and Il-4.

Figure 3A:
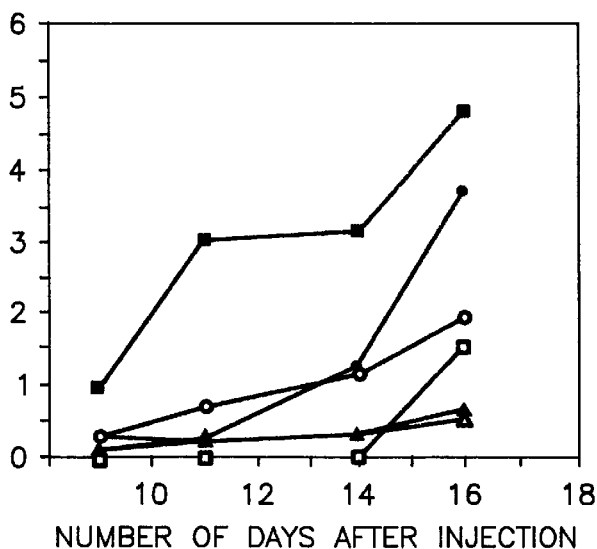
Figure 3B:
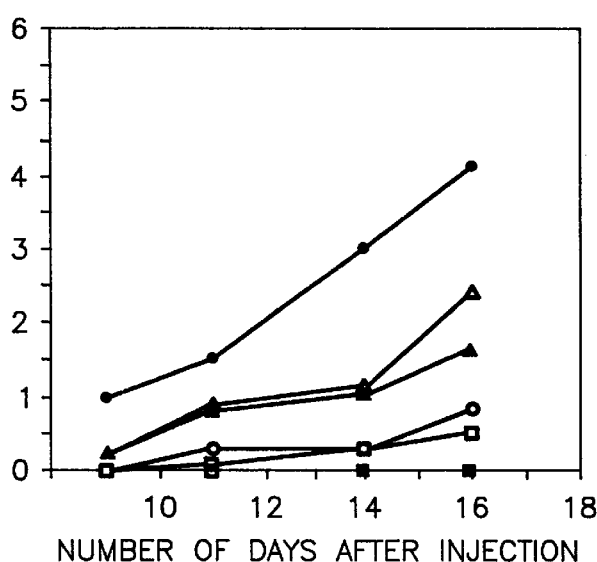
Figure 3C:
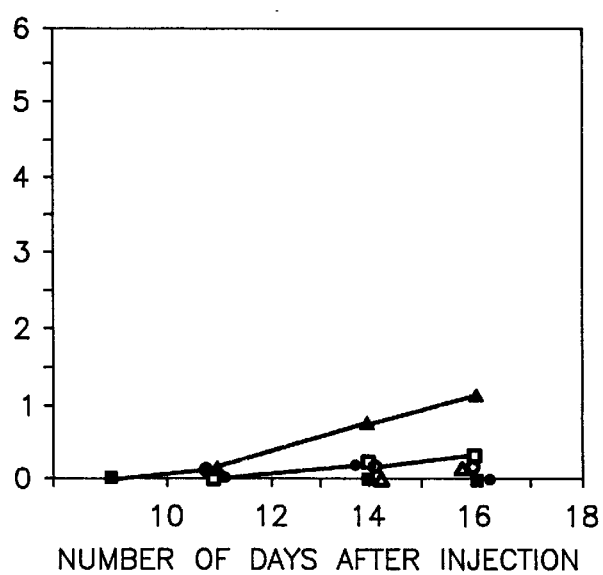

FIGS. 3A to 3C concern the growth of Lewis tumors (y-axis) in C57B1/6 mice as a function of days post injection (x-axis): after inoculation by Lewis tumor cells alone (FIG. 3A), Lewis tumor cells in the presence of non-transfected rMTC (FIG. 3B), and rMTC transfected by IL-2 (FIG. 3C).

EXAMPLE 1

Use of allogenic cells secreting IL-2

Transformed L cells of H-$2^k$ haplotype expressing Il-2 and called LMI (IL-2) were isolated.

The LMI cell line of mice expresses the ICAM-1 adhesion molecule and is derived from L cells described in French Patent No.80.09.041.

The LMI line was described by Christian Jaulin (Analyse structurale et fonctionnelle des antigènes d'histocompatibilité de classe I, doctoral Thesis at the Université de Paris IX, 1991).

DBA/2 mice of H-$2^d$ haplotype are injected with a mixture of $5·10^5$ P815 cells and $10^6$ or $5·10^6$ LMI (IL-2) cells.

FIGS. 1A to 1E illustrate the results obtained.

These figures show that the allogenic LMI cells expressing IL-2 confer higher protection against the growth of co-injected P815 cells than that conferred by LMI cells not expressing IL-2.

The operating conditions of FIGS. 1A to 1E are the following:

FIG. 1A, $5·10^5$ P815 cells,

FIG. 1B, $5·10^5$ P815+$10^6$ L cells,

FIG. 1C, $5·10^5$ P815+$5·10^6$ L cells,

FIG. 1D, $5·10^5$ P815+$10^6$ LMI (IL-2) cells,

FIG. 1E, $5·10^5$ P815+$5·10^6$ LMI (IL-2) cells,

Of the five mice corresponding to FIG. 1D, two are totally protected, one developed a tumor very late, and the remaining two developed tumors rapidly.

In the operating conditions of FIG. 1E, a single mouse formed a tumor rapidly, whereas the other four were totally protected.

In FIGS. 1A to 1E, the figures indicated on the x-axis correspond to the number of days post injection, whereas the y-axis indicates the volume of the tumor in cm$^3$.

EXAMPLE 2

Effect of allogenic cells secreting interleukins against Lewis tumors $5 \cdot 10^5$ isolated cells of freshly-implanted Lewis tumors (H-$2^b$ haplotype) mixed with different quantities of P815 (IL-2) or of P815 (IL-4) are injected into C57B1/6 mice(H-$2^b$ haplotype).

The P815 cells are H-$2^d$ haplotype.

Figure 2H:
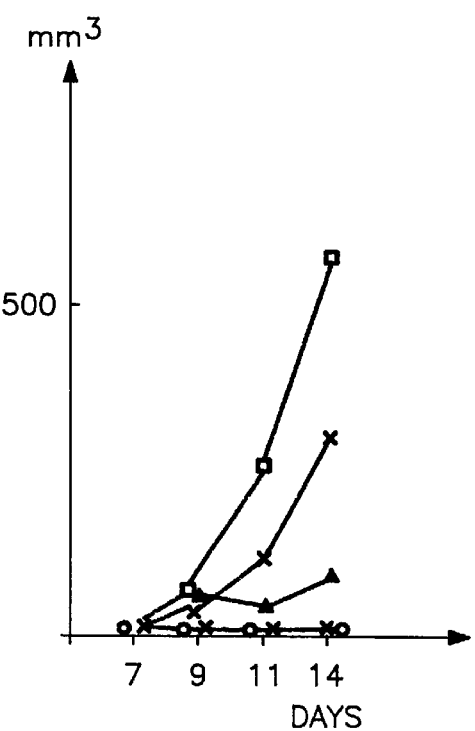
Figure 2I:
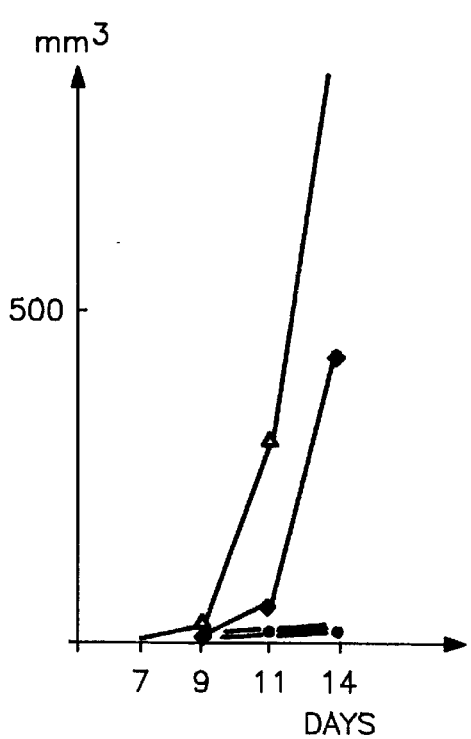

FIGS. 2A to 2I were obtained in the following conditions:

FIG. 2A, $5 \cdot 10^5$ Lewis cells,

FIG. 2B, $5 \cdot 10^5$ Lewis cells+$5 \cdot 10^6$ P815 cells,

FIG. 2C, $5 \cdot 10^5$ Lewis cells+$10^6$ P815 cells,

FIG. 2D, $5 \cdot 10^5$ Lewis cells+$2 \cdot 10^6$ P815 cells,

FIG. 2E, $5 \cdot 10^5$ Lewis cells+$5 \cdot 10^5$ P815 cells,

FIG. 2F, $5 \cdot 10^5$ Lewis cells+$10^6$ P815 (IL-2) cells,

FIG. 2G, $5 \cdot 10^5$ Lewis cells+$2 \cdot 10^6$ P815 (IL-2) cells,

FIG. 2H, $5 \cdot 10^5$ Lewis cells+$10^6$ P815 (IL-4) cells,

FIG. 2I, $5 \cdot 10^5$ Lewis cells+$5 \cdot 10^5$ P815 (IL-2) cells+$5 \cdot 10^5$ P815 (IL-4) cells.

In these figures, the x-axis indicates the number of days post treatment, and the y-axis indicates the volume of the tumors expressed in mm$^3$.

These results ensure that the P815 (IL-2) cells confer a high and reproducible protection, whereas the non-transfected P815 cells do not confer this type of protection.

The P815 (IL-4) cells (FIG. 2H) also confer protection, but less than that conferred by the P815 (IL-2) cells.

However, no synergy was observed between the effect of the P815 (IL-2) cells and the effect of the P815 (IL-4) cells (FIG. 2I), but, on the contrary, a rather antagonistic effect.

EXAMPLE 3

Rejection of Lewis tumors in C57B1/6 mice induced by tumor cells secreting interleukin-2

Medullary thyroid carcinoma of the rat (rMTC) is a spontaneous neoplasm derived from intra-thyroid C cells secreting calcitonin. The specific cell line obtained from these cells (rMTC 6.23) has been described (Zeytinoglu et al, Endocrinology, 107 509 (1980)).

The capacity of this strain secreting large quantities of interleukin-2 (5000 UI/ml$\cdot 10^6$ cells per 24 h) to induce antitumor immune protection in a xenogenic host has been tested. C57B1/6 mice were inoculated with either $2 \cdot 5 \cdot 10^5$ Lewis tumor cells alone, or with these cells in combination with $10^6$ rMTC (IL-2) rat cells.

The xenogenic cells secreting interleukin-2 induce significant protection, as shown by FIG. 3.

FIG. 3A concerns the subcutaneous inoculation of six C57B1/6 mice with $2.5 \cdot 10^6$ Lewis tumor cells alone.

FIGS. 3B and 3C correspond respectively to the combination of $2.5 \cdot 10^5$ Lewis cells with $10^6$ non-transfected rMTC cells (FIG. 3B), or with $10^6$ rMTC cells transfected by interleukin-2 (FIG. 3C).

All the animals without tumors on the sixth day post injection did not develop any tumor after 60 days.

However, despite the demonstration of significant protection, it is nevertheless necessary in the same conditions to add four times more xenogenic cells secreting interleukin-2 than allogenic cells.

EXAMPLE 4

Influence of the presence of NK-1.1 cells on the rejection of tumors

The effect of the selective elimination in vivo of Natural Killer (NK) cells on the rejection of tumors in C57B1/6 mice co-innoculated with Lewis tumor cells and allogenic P815 (IL-2) cells was tested.

The elimination in vivo by the antibodies was carried out by intra-peritoneal injection of 100 µg of purified NK-specific monoclonal antibody, during three days, starting one day after the injection of the tumor cells.

The effectiveness of the elimination of the NK cells was assessed by a chromium 51 sorting-out test using YAC1 target cells (Kiessling et al, Eur.J.Immunol., 5 112 (1975)), as described by Koo et al (J.Immunol., 137 3742 (1986)).

It was confirmed that the treatment was effective on the Natural Killer activities endogenous and induced by Poly-IC of the YAC1 cell line in the spleen of the treated animals.

The results are summarized in Table 1 below.

By comparison with untreated animals, the tumors grow more rapidly in mice into which anti-NK antibodies have been injected. Moreover, the evaluation of tumor protection shows that the mice from which the NK-1.1 cells were eliminated by an antibody treatment were incapable of inhibiting the tumor growth of Lewis cells (Table 1).

It must nevertheless be observed that the inoculation of allogenic cells secreting lymphokines into these treated animals causes a delay in the appearance of the tumors, and a decrease in their average volume.

EXAMPLE 5

Study of the rejection of Lewis tumor cells by mice who have previously rejected tumor cells of the same type Three groups of C57B1/6 mice, on which experiments were already conducted on the rejection of Lewis tumor cells co-innoculated with P815 (IL-2) cells, were tested six weeks after the first rejection with Lewis tumor cells ($5 \cdot 10^5$).

None of the mice tested survived these injections. However, it was observed that tumor growth was slightly delayed in comparison with the growth in the control animals who had not been previously treated with Lewis tumor cells and P815 (IL-2) cells.

In conclusion, these overall results have served to demonstrate:

that therapy by cells expressing interleukin genes is feasible for spontaneous tumors, and not only for chemically-induced tumors as described in the prior art, the use of allogenic cells is feasible, and permits the rejection of the tumors, the delivery by transient expression of a biologically-active substance is feasible, allogenic cells or partially-allogenic cells can be used as carriers of a foreign antigen to the host capable of inducing an immune reaction of the tumoral or cellular type, the 'Natural Killer' (NK) cells are implicated in the protection induced by IL-2 expressed by the allogenic cells.

TABLE 1

Growth of Lewis tumors in C57B1/6 mice treated with an anti-NK 1.1* monoclonal antibody

| treatment in vivo** | parental tumor | allogenic cells (5 · 10⁵) | average volume of tumor (cm³) D1+ | D2++ | fraction of animals protected+++ |
|---|---|---|---|---|---|
| — | Lewis | — | 0.11 ± 0.07 | 1.76 ± 0.42 | 0/5 |
| anti-NK 1.1 | Lewis | — | 0.25 ± 0.18 | 2.20 ± 0.60 | 0/5 |
| anti-NK 1.1 | Lewis | P815 | 0.42 ± 0.20 | 2.30 ± 0.58 | 0/5 |
| anti-NK 1.1 | Lewis | P815 (IL-2) | 0.12 ± 0.15 | 2.00 ± 0.70 | 0/5 |
| anti-NK 1.1 | Lewis | P815 (IL-4) | 0.14 ± 0.22 | 2.80 ± 1.70 | 0/5 |
| anti-NK 1.1 | Lewis | P815 (IL-2) P815 (IL-4) | 0 | 1.30 ± 0.40 | 0/5 |

*The percentage of specific salting-out of $^{51}Cr$ chromium after incubation of the target cells for 4 h at 37° C. is negligible for the treated animals, whereas, in the spleen cells induced by Poly-IC, it is 54 and 23% after 1 day and 8 days respectively after treatment in vitro with a target cell: effector cell ratio of 1/100.
**The treatment was carried out using the antibody described by Koo and Peppard (Hybridoma, 3301 (1984)).
+Measurement of tumor volume 9 days after inoculation of C57B1/16 mice.
++Measurement of tumoral volume 16 days after inoculation of C57B1/6 mice.
+++The fraction of the animals protected measured is the fraction of animals without detectable tumors 30 days after inoculation.

What we claim is:

1. A method of treating a malignant tumor in a subject comprising:
    (a) obtaining cells which are allogeneic or xenogeneic relative to the subject,
    (b) modifying said cells by transfection with DNA encoding at least one immunomodulator, whereby the cells secrete said immunomodulator,
    (c) administering to the tumor a plurality of the modified cells of step(b), so that the modified cells secrete said immunomodulator so as to inhibit proliferation of the malignant tumor in the subject.

2. The method of claim 1 wherein said cells are allogeneic relative to the subject.

3. The method of claim 1 wherein said cells are xenogeneic relative to the subject.

4. The method of claim 1 wherein the immunomodulator is selected from the group consisting of IL-2, IL-4, TNF, gamma interferon and GM-CSF.

5. The method of claim 1 wherein the cells are modified to secrete more than one immunomodulator.

6. A method of claim 1 wherein the cells are sensitive to a drug promoting their elimination from the subject.

7. A method of claim 6 wherein the drug is gancyclovir, and the cells are transfected with the thymidine-kinase gene.

8. A method of claim 1 wherein the cells are transfected with a gene encoding a dye marker.

9. A method of claim 1 wherein the cells also possess genes enabling them to secrete specific antigens of a cancer or other tumor.

10. A method of claim 1 wherein said plurality of a modified cells is composed of different cell types, each secreting an immunomodulator or an antigen specific to a tumor.

11. A method of claim 1 wherein the cells express genes enabling them to secrete in vivo an antigen capable of inducing an immune reaction of the humoral or cellular type.

12. A method of claim 11 wherein the cells express genes enabling them to secret in vivo a specific antigen of a tumor, an antigen involved in an auto-immune disease, an antibody or a derivative of an antibody.

13. A method of claim 1 wherein the cells are monkey cells.

14. A method of claim 13 wherein the monkey cells are VERO cells.

15. A method of treating a malignant tumor in a subject comprising:
    a) obtaining cells which are allogeneic or xenogeneic relative to the subject,
    b) modifying said cells by transfection with DNA encoding at least one immunomodulator, whereby the cells secrete said immunomodulator,
    c) administering to the subject a plurality of the modified cells of step (b), so that the modified cells secrete said immunomodulator so as to inhibit proliferation of the malignant tumor in the subject.

16. A method of treating a caner or a tumor in a subject comprising:
    a) obtaining cells which are allogeneic or xenogeneic relative to the subject,
    b) modifying said cells by transfection with DNA encoding at least one immunomodulator, whereby the cells secrete said immunomodulator,
    c) administering to the subject a plurality of the modified cells of step (b), so that the modified cells secrete said immunomodulator so as to inhibit proliferation of the cancer or the tumor in the subject.

17. A method of claim 16 wherein said cells are allogeneic relative to the subject.

18. A method of claim 16 wherein said cells are xenogeneic relative to the subject.

19. A method of claim 16 wherein the immunomodulator is selected from the group consisting of IL-2, IL-4, TNF, gamma interferon and GM-CSF.

20. A method of claim 16 wherein the cells are modified to secrete more than one immunomodulator.

21. A method of claim 16 wherein the cells are sensitive to a drug promoting their elimination from the subject.

22. A method of claim 21 wherein the drug is gancyclovir, and the cells are transfected with the thymidine-kinase gene.

23. A method of claim 16 wherein the cells are transfected with a gene encoding a dye marker.

24. A method of claim 16 wherein the cells also possess genes enabling them to secrete specific antigens of a cancer or other tumor.

25. A method of claim 16 wherein said plurality of modified cells is composed of different cell types, each secreting an immunomodulator or an antigen specific to a tumor.

26. A method of claim 16 wherein the cells express genes enabling them to secrete in vivo an antigen capable of inducing an immune reaction of the humoral or cellular type.

27. A method of claim 16 wherein the cells express genes enabling them to secrete in vivo a specific antigen of a tumor, an antigen involved in an auto-immune disease, an antibody or a derivative of an antibody.

28. A method of claim 16 wherein the cells are monkey cells.

29. A method of claim 28 wherein the monkey cells are VERO cells.

* * * * *